United States Patent [19]

Busker et al.

[11] Patent Number: 4,469,875

[45] Date of Patent: Sep. 4, 1984

[54] OPTICALLY ACTIVE PROLINE DERIVATIVE, PROCESS FOR ITS PRODUCTION AND USE

[75] Inventors: Eberhard Busker, Pulheim; Jürgen Martens, Alzenau; Regina Steigerwald, Blankenbach; Horst Weigel, Rodenbach, all of Fed. Rep. of Germany

[73] Assignee: Degussa Aktiengesellschaft, Frankfurt, Fed. Rep. of Germany

[21] Appl. No.: 426,132

[22] Filed: Sep. 28, 1982

[30] Foreign Application Priority Data

Nov. 4, 1981 [DE] Fed. Rep. of Germany ....... 3143726

[51] Int. Cl.³ ................ C07C 207/00; C07C 207/12; B01D 15/08
[52] U.S. Cl. .................... 548/532; 210/656; 210/198.2; 548/201; 548/535; 562/402
[58] Field of Search ...................... 548/532, 201, 535; 562/402; 210/656, 198.2

[56] References Cited

U.S. PATENT DOCUMENTS

| | | | |
|---|---|---|---|
| 2,794,025 | 5/1957 | Amiard et al. | 548/532 |
| 3,282,917 | 11/1966 | Magerlein | 548/532 X |
| 3,393,201 | 7/1968 | Preau | 548/532 X |
| 4,133,753 | 1/1979 | Takeuchi et al. | 548/532 X |

FOREIGN PATENT DOCUMENTS

| | | | |
|---|---|---|---|
| 1562512 | 4/1969 | France | 210/656 |
| 1562513 | 4/1969 | France | 210/656 |
| 914548 | 3/1982 | U.S.S.R. | 210/656 |

OTHER PUBLICATIONS

Iskandarani, et al., Analytical Chemistry, 53 (3), Mar. 1981, pp. 489–495.
C.A., 86: 90208b, (1977); Crooks, et al.
C.A., 95: 23008j, (1981); Moll, et al.
Noller, Chemistry of Carbon Compounds, 3rd Ed., (1965), pp. 813–814, W. B. Saunders Co., Phila., Penna., U.S.A.

Lindner; Chimia, vol. 82, pp. 294–307, (1981).
Davankov, et al., Chromatographia, vol. 13, pp. 677–685, (1980).

Primary Examiner—Joseph Paul Brust
Attorney, Agent, or Firm—Cushman, Darby & Cushman

[57] ABSTRACT

The invention is directed to optically active proline derivative of the general formula:

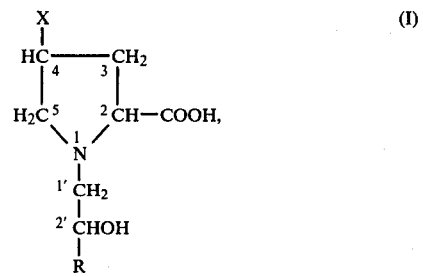

in which X is a hydrogen atom or a hydroxyl group and R is a hydrogen atom, an unsubstituted or alkyl group substituted phenyl group or a straight chain or branched alkyl group having 1 to 20 carbon atoms and a process for its production by reacting an enantiomerically pure proline or 4-hydroxy-proline as a solution in an alkanol having 1 to 4 carbon atoms with 0.9 to 2 times the molar amount of an alkali metal alcoholate corresponding to the alkanol and 1 to 3 times the molar amount of an epoxide of the general formula

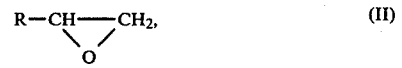

in which R is as defined above. The optically active proline derivative of general formula (I) can be used in the form of metal ion chelate complexes as the chiral stationary phase in the separation of enantiomers by means of liquid chromatography.

17 Claims, No Drawings

OPTICALLY ACTIVE PROLINE DERIVATIVE, PROCESS FOR ITS PRODUCTION AND USE

SUMMARY OF THE INVENTION

The subject matter of the invention is optically active proline derivatives of the general formula:

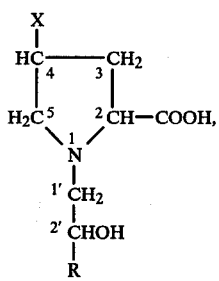

in which X is a hydrogen atom or a hydroxyl group and R is a hydrogen atom, an unsubstituted or alkyl group substituted phenyl group, e.g. methyl phenyl, ethyl phenyl, butylphenyl, t-butylphenyl, amylphenyl, or a straight chain or branched alkyl group having 1 to 20 carbon atoms, e.g. methyl, ethyl, butyl, sec.butyl, isodecyl, decyl, eicosanyl, and a process for its production by reacting an enantiomerically pure proline or 4-hydroxy-proline as a solution in an alkanol having 1 to 4 carbon atoms, e.g. methanol, ethanol, isopropanol, butanol, sec.butanol with 0.9 to 2 times the molar amount of an alkali metal alcoholate corresponding to the alkanol, e.g. sodium methylate, sodium ethylate, potassium methylate, potassium ethylate, sodium isopropylate, and 1 to 3 times the molar amount of an epoxide of the general formula:

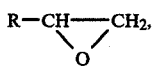

in which R is as defined above.

The optically active proline derivative of general formula (I) can be used in the form of metal ion chelate complexes as the chiral stationary phase in the separation of enantiomers by means of liquid chromatography.

Therefore a further subject matter of the invention is the use of the optically active proline derivatives of general formula (I) in the form of metal ion-chelate complexes as chiral stationary phase in the separation of enantiomers by means of liquid chromatography.

Particularly important and valuable are those optically active proline derivatives of the general formula (I) in which the carbon atom in the 2-position has the (S)-configuration and in the case where X=OH the carbon in the 4-position has the (R)-configuration. For the case where in general formula (I) R has a meaning other than hydrogen then the carbon atom in the 2'-position has the (RS)-, (S)- or (R)-configuration.

For the production of the optically active proline derivative there is dissolved enantiomerically pure proline or 4-hydroxy-proline in an alkanol having 1 to 4 carbon atoms and it is reacted with an alkali metal alcoholate corresponding to the alkanol and the epoxide of general formula (II).

The alkanol employed can be primary, secondary or tertiary and straight chain or branched. Preferably there is used methanol or ethanol. Further suitable alkanols include n-propanol, isopropyl alcohol, n-butanol, secondary butanol, isobutyl alcohol, and tertiary butyl alcohol. The alkanol is employed in an amount between 0.5 and 5 liters, preferably between 1 and 2 liters, per mole of proline or 4-hydroxy-proline.

The alkali metal alcoholate corresponding to the alkanol employed, preferably the sodium or potassium alcoholate, is employed in an amount between 0.9 and 2 moles, preferably 1 mole per mole of proline or 4-hydroxy-proline. It can be added as such or formed in situ by dissolving the alkali metal or the alkali metal hydroxide in the alkanol.

The epoxide of general formula (II) is employed in an amount between 1 and 3 moles, preferably 1 to 2 moles, especially 1 mole, per mole of proline or 4-hydroxy-proline. Examples of usable epoxides of general formula (II) are ethyleneoxide, 1,2-epoxy-propane, 1,2-epoxy-butane, 1,2-epoxy-hexane, 1,2-epoxy-octane, 1,2-epoxy-decane, 1,2-epoxy-dodecane, 1,2-epoxy-tetradecane, 1,2-epoxy-hexadecane, 1,2-epoxy-octadecane, 1,2-epoxy-eicosane, styrene oxide or ring methyl substituted styrene oxide, e.g. p-methyl styrene oxide, o-methyl styrene oxide, and m-methyl styrene oxide and p-ethyl styrene oxide.

The reaction takes place generally at normal pressure. The reaction temperature can be between 0° and 150° C., preferably between 15° C. and the boiling temperature of the reaction mixture.

The optically active proline derivative formed [general formula (I)] can be recovered by neutralization of the reaction mixture, separating off crystallized alkali metal salt and distilling off the alkanol. Alternatively it can also be isolated by adsorption of the alkali metal ions on a weakly acid ion exchanger and concentration of the neutral eluate. In many cases it is also advantageous to treat the reaction mixture with water and to separate off the optically active proline derivative of general formula (I) crystallizing out.

In the optically active proline-derivatives of general formula (I) formed, if R is other than hydrogen, then the carbon atom in the 2'-position can have the (RS)-configuration. It is present then, with uniform configuration of the carbon atoms in the 2-position and in a given case, in the 4-position, as a mixture of two diastereomers. For example, starting from (S)-proline and 1,2-epoxy-tetradecane there is obtained a mixture of the two compounds which are diastereomers to each other, (2'S,2S)-N-(2-hydroxytetradecyl)-proline and (2'R, 2S)-N-(2-hydroxy-tetradecyl)-proline. Such a mixture of diastereomers can, for example, be separated through fractional crystallization and thus there be produced the enantiomerically pure, sterically uniform products.

The separation of such a diastereomer mixture, however, generally is not required at all because even the mixture in the form of metal ion-chelate complexes as chiral stationary phase in racemate separations is surprisingly more stereo selective than known enantiomerically pure metal ion-chelate complexes.

For use of the optically active proline derivatives of general formula (I) in the form of metal ion-chelate complexes as chiral stationary phase in the separation of enantiomers by means of liquid chromatography according to the invention a column having silanized silica gel is coated with the proline derivatives. The coating takes place in known manner, as is described for example, in Chromatographia Vol. 13, pages 677 to 684 (1980). Then subsequently through adsorption of a suitable metal ion there is formed a chelate complex. As metal ions there are used, e.g. $Cu^{2+}$, $Ni^{2+}$, $Zn^{2+}$, $Cd^{2+}$, $Hg^{2+}$, or $Co^{3+}$. Especially preferred is the use of $Cu^{2+}$.

The basis of the chiral ligand exchange chromatography produces complexation models of metal ions and optically active chelate formers, whereby both the selector, here an optically active proline derivative of general formula (I), and also the selectand must exhibit chelate ring forming structure characteristics. There is then the development of mixed chelate complexes with two dissimilar optically active ligands. The entire complexes therefore are assigned diastereomeric properties. A good enantiomer selectivity then is attained if the kinetics of the association and dissociation process are sufficiently different in the ligand exchange for the two diastereomer pairs.

The metal ion-chelate complexes of the optically active proline derivative of general formula (I) for example, show a very high enantioselectivity ($\alpha$ value) in the racemate separation of $\alpha$-amino-carboxylic acids. In this connection they are superior to the chiral stationary phases known from Chimia Vol. 82, pages 294 et seq. (1981).

A particular industrial advantage of the optically active proline derivatives of general formula (I) is that they are very readily accessible. The production of the metal ion-chelate complex therefore is substantially simpler than the production of other selectors used for the same purpose.

With the help of the metal ion-chelate complexes of the optically active proline derivatives of general formula (I) for the first time racemic thiazolidin-4-carboxylic acids have been resolved into the antipodes with outstanding enantio-selectivity. Also it permits for example simultaneous resolution of mixtures of the stereoisomers of an aminocarboxylic acid and its acyl derivatives into the (R)-aminocarboxylic acid, the (S)-aminocarboxylic acid, the N-acyl-(R)-aminocarboxylic acid and the N-acyl-(S)-aminocarboxylic acid. The metal ion-chelate complexes of the optically active proline derivatives of general formula (I) therefore are also outstandingly suitable as stationary phase in the simultaneous liquid chromatographic separation of structural and stereiosomers even of different classes of compounds. However, there can also be separated simultaneously the stereoisomers of different members of the same class of compounds, for example, the aminocarboxylic acids, especially the $\alpha$-aminocarboxylic acids.

Specific metal ion-chelate complexes of the optically active proline derivatives of general formula (I) besides being used for racemate separation can also be used as catalysts for the production of chiral compounds by asymmetrical hydrogenation of prochiral compounds.

The optically active proline derivatives of general formula (I), when R is sufficiently large, finally have surface-activ properties.

Unless otherwise indicated all parts and percentages are by weight.

The compositions can comprise, consist essentially of, or consist of the stated materials and the process can comprise, consist essentially of, or consist of the stated steps with the materials set forth.

The invention will be explained in more detail through the following examples.

DETAILED DESCRIPTION

EXAMPLE 1

57.6 grams of (2S)-proline (0.5 mole) were dissolved in 800 ml of methanol which contained 0.5 mole of sodium methylate. After addition of 106 grams (0.5 mole) of 1,2-epoxy-tetradecane the solution was allowed to stand for 20 hours at room temperature.

The pH was adjusted to 6 with methanolic hydrochloric acid and the sodium chloride which crystallized out was filtered off. After distilling off the methanol there remained an oily residue which upon stirring with 700 ml of acetone crystallized. There were obtained 146.5 grams (89.6% of theory) of colorless crystals of (2S, 2'RS)-N-(2-hydroxy-tetradecyl)-proline. The melting range of the mixture of diastereomers was 99°–118° C.

| $C_{19}H_{37}NO_3$ | Elemental Analysis: | | |
|---|---|---|---|
| | C | H | N |
| Found: | 69.51% | 11.20% | 4.15% |
| Calculated: | 69.68% | 11.39% | 4.28% |

$[\alpha]_D^{20} = -30.5°$ (c=1; methanol).

A commercial chromatography column for high pressure liquid chromatography (4.6×250 mm); filled with silica gel particles modified by octylsilane and having an average particle size of 10 μm was first conditioned with a mixture of 15 volume percent methanol and 85 volume percent water. Then there was flushed through the column 2 ml of a methanolic solution of 50 mg of the above diastereomer mixture at a flow of 0.5 ml/minute. Subsequently there was pumped through the column 2 ml of a saturated solution of copper II acetate in a mixture of 15 volume percent methanol and 85 volume percent water. Excess salt was removed by rinsing with 100 ml of a mixture of 15 volume percent methanol and 85 volume percent water which contained $1 \times 10^{-4}$ mole of copper II acetate.

There were injected on the thus coated column 5 μl of a 0.1 weight percent solution of racemic thiazolidin-4-carboxylic acid. There served as mobile phase a mixture of 15 volume percent methanol and 85 volume percent of a $10^{-4}$ molar aqueous copper II acetate solution. There was established a flow of 2 ml/minute. The separation took place at room temperature with a selectivity of $\alpha = 2.1$.

EXAMPLE 2

The procedure was as in Example 1. As epoxide there was employed 120. 1 grams (0.5 mole) of 1,2-epoxy-hexadecane. There were obtained 164.4 grams (92.5% of theory) of colorless crystals of (2S, 2'RS)-N-(2-hydroxy-hexadecyl)-proline. The melting range of the mixture of diastereomers was 145°–170° C.

| $C_{21}H_{41}NO_3$ | Elemental Analysis: | | |
|---|---|---|---|
| | C | H | N |
| Found: | 70.83% | 11.71% | 3.98% |
| Calculated: | 70.94% | 11.62% | 3.94% |

$[\alpha]_D^{20} = -27.7°$ (c=0.5; methanol).

EXAMPLE 3

2.3 grams (0.1 mole) of sodium were dissolved in 150 ml of methanol. After addition of 11.5 grams (0.1 mole) of (2S)-proline and 20.2 grams of 1,2-epoxydodecane (0.1 mole) the solution was boiled under reflux for 2 hours.

After cooling the solution was led through a column containing 100 ml of a weakly acid ion exchange resin (Lewatit CN P 80) and the neutral eluate was concentrated to 55 grams. Through fractional crystallization by portionwise addition of diethyl ether there was achieved a separation of the two diastereomers of (2S)-N-(2-hydroxy-dodecyl)-proline. High melting form:

M.P.=138°-139° C.

$[\alpha]_D^{25} = -14.7°$ (c=0.5; ethanol).

T.L.C.: n-butanol:methanol: $H_2O=4:5:1$ silica gel $R_f=0.51$.

Lower melting form: M.P.=118°-120° C.

$[\alpha]_D^{25} = -35.8°$ (c=1; ethanol).

T.L.C.: n-butanol:methanol:$H_2O=4:5:1$ Silica gel $R_f=0.42$.

EXAMPLE 4

34.5 grams of (2S)-proline (0.3 mole) were dissolved in 400 ml of methanol which contained 16.2 grams of sodium methylate (0.3 mole). After addition of 54 grams of styrene oxide (0.45 mole) the temperature slowly increased around 5° C.

After standing for 20 hours at room temperature the clear solution was led through a column containing 250 ml of a weakly acid ion exchanger, (Lewatit CNP 80). The neutral eluate was evaporated at reduced pressure. The oily residue crystallized on stirring with acetone. There were obtained 28.3 grams of colorless crystals of (2S, 2'RS)-N-(2-hydroxy-2-phenyl-ethyl)-proline. The mixture of diastereomers melted at 165°-181° C.

| $C_{13}H_{17}NO_3$ | Elemental Analysis: | | |
|---|---|---|---|
| | C | H | N |
| Found: | 66.22% | 7.29% | 5.78% |
| Calculated: | 66.36% | 7.28% | 5.95% |

$[\alpha]_D^{20} = -55.8°$ (c=0.5; methanol).

EXAMPLE 5

34.5 grams of (2S)-proline (0.3 mole) and 12 grams of sodium hydroxide were dissolved in 600 ml of methanol and cooled to 10° C. After addition of 15.9 grams (0.36 mole) of ethylene oxide the solution was allowed to stand for 20 hours at room temperature. On neutralization the product crystallized out and was once again recrystallized from methanol.

There were obtained 29.7 grams of colorless crystals of (2S)-N-(2-hydroxy-ethyl)-proline.

M.P.=199°-200° C.

| $C_7H_{14}NO_3$ | Elemental Analysis: | | |
|---|---|---|---|
| | C | H | N |
| Found: | 52.89% | 8.11% | 8.69% |
| Calculated: | 52.81% | 8.22% | 8.80% |

$[\alpha]_D^{20} = -67.9°$ (c=2; water).

EXAMPLE 6

The procedure was as in Example 5 but in place of (2S)-proline there were employed 39.3 grams of (2S, 4R)-4-hydroxy-proline (0.3 mole). There were obtained 35.4 grams (67.4% of theory) of colorless crystals of (2S, 4R)-N-(2-hydroxyethyl)-4-hydroxy-proline.

M.P.=202°-204° C.

| $C_7H_{13}NO_4$ | Elemental Analysis: | | |
|---|---|---|---|
| | C | H | N |
| Found: | 47.97% | 7.43% | 7.89% |
| Calculated: | 47.99% | 7.48% | 8.00% |

$[\alpha]_D^{20} = -78.0°$ (c=2; water).

EXAMPLE 7

78.6 grams of (2S, 4R)-4-hydroxy-proline (0.6 mole) were dissolved in 1 liter of methanol which contained 32.4 grams of sodium methylate. After addition of 76.8 grams of 1,2-epoxy-octane (0.6 mole) the solution was allowed to stand for 20 hours. Then the pH was adjusted to 6 with hydrochloric acid and the methanol distilled off. The residue was recrystallized from 300 ml of water. There were obtained 130.7 grams (84.1% of theory) of colorless crystals of (2S, 4R, 2'RS)-N-(2-hydroxy-octyl)-4-hydroxy-proline.

The melting range of the mixture of diastereomers was 132°-140° C.

| $C_{13}H_{25}NO_4$ | Elemental Analysis: | | |
|---|---|---|---|
| | C | H | N |
| Found: | 60.13% | 9.63% | 5.28% |
| Calculated: | 60.20% | 9.72% | 5.40% |

$[\alpha]_D^{20} = -50.5°$ (c=1; methanol).

EXAMPLE 8

The process was as in Example 7. As epoxide there was employed 93.6 grams of 1,2-epoxy-decane (0.6 mole). After recrystallization from 900 ml of water there were obtained 155.3 grams (90% of theory) of colorless crystals of (2S, 4R, 2'RS)-N-(2-hydroxy-decyl)-4-hydroxy-proline.

The melting range of the mixture of diastereomers was 145°-154° C.

| $C_{15}H_{29}NO_4$ | Elemental Analysis: | | |
|---|---|---|---|
| | C | H | N |
| Found: | 62.65% | 10.03% | 4.78% |
| Calculated: | 62.68% | 10.17% | 4.87% |

$[\alpha]_D^{20} = -47.8°$ (c=1; methanol).

EXAMPLE 9

The process was as in Example 7. As epoxide there was employed 110.4 grams of 1,2-epoxy-dodecane (0.6 mole). After the reaction there were added 1.5 liters of water and the mixture adjusted with hydrochloric acid to pH 6. Thereby the (2S, 4R, 2'RS)-N-(2-hydroxy-dodecyl)-4-hydroxy-proline crystallized out. After filtering off with suction 177.8 grams (93.7% of theory) of colorless crystals were obtained.

The melting range of the mixture of diastereomers was 98°-106° C.

| Elemental Analysis: | | | |
|---|---|---|---|
| $C_{17}H_{33}NO_4$ | C | H | N |
| Found: | 64.69% | 10.49% | 4.39% |
| Calculated: | 64.72% | 10.54% | 4.44% |

$[\alpha]_D^{20} = -42.2°$ (c=0.5; methanol).

As described in Example 1 there was coated a commercial chromatography column with the above mixture of diastereomers.

By means of a loop injector there were injected 10 μl of a 0.1 weight percent aqueous solution of racemic thiazolidine-4-carboxylic acid on the thus coated column. The column was thermostated at 50° C. by means of a water bath jacket. As mobile phase there was flushed through the column a mixture of 15 volume percent methanol and 85 volume percent of a $10^{-4}$ molar copper II acetate solution in water having a flow of 2 ml/minute. After 6 minutes the L-thiazolidin-4-carboxylic acid was eluted, after 18 minutes the D-thiazolidine-4-carboxylic acid. The detection of the materials was carried out with a UV detector of variable wave length at wave lengths of 235 mm.

There was split a mixture of N-acetyl-DL-methionine and DL methionine with the same column. As mobile phase there was flushed through the column a mixture of 10 volume percent methanol and 90 volume percent of a $10^{-4}$ molar copper II acetate solution in water having a flow of 3 ml/minute. There were observed the following retention times:

N-Acetyl-L-methionine: 2.4 minutes
N-Acetyl-D-methionine: 2.7 minutes
L-Methionine: 6.8 minutes
D-Methionine: 9.4 minutes In the manner described for the separation of the racemic thiazolidin-4-carboxylic acid there can also be resolved the following racemic aminocarboxylic acids: arginine, aspartic acid, asparagine, alanine, 4,4-dimethyl-thiazolidine carboxylic acid, glutamine, isoleucine, leucine, lysine, phenylalanine, proline, serine, and threonine.

EXAMPLE 10

Example 1 was repeated with the difference that in place of methanol there were employed 1000 ml of ethanol and in place of sodium methylate 0.5 mole of sodium ethylate. There were obtained 150 grams (91.7% of theory) of the mixture of diastereomers from (2S, 2'S)-N-(2-hydroxy-tetradecyl)-proline and (2S, 2'R)-N-(2-hydroxy-tetradecyl)-proline.

EXAMPLE 11

Example 10 was repeated with the difference that in place of ethanol there were employed 1000 ml of tert.butanol and in place of the sodium methylate 0.5 mole of potassium tert.-butylate. There were obtained 141 grams (86.2% of theory) of colorless crystals of the mixture of diastereomers.

EXAMPLE 12

Example 7 was repeated with the difference that in place of the 1,2-epoxy-octane there were employed 127.2 grams (0.6 mole) of 1,2-epoxy-tetradecane. After the end of the reaction there was added to the reaction mixture 1.5 liters of water and the pH adjusted to 6 with hydrochloric acid. Thereby the (2S, 4R, 2'RS)-N-(2-hydroxy-tetradecyl)-4-hydroxy-proline crystallized out. After filtering with suction, washing with water, and drying there were obtained 185.1 grams (90% of theory) of colorless crystals.

The melting range of the mixture of diastereomers was 136°–154° C.

| Elemental Analysis: | | | |
|---|---|---|---|
| $C_{19}H_{37}NO_4$ | C | H | N |
| Found: | 66.09% | 10.65% | 4.10% |
| Calculated: | 66.43% | 10.86% | 4.07% |

$[\alpha]_D^{20} = -36.8°$ (c=0.5; methanol).

A commercial chromatography column was coated with the above diastereomer mixture in the manner described in Example 1.

The thus coated column under the conditions given in Example 1 separated racemic proline with a selectivity of $\alpha = 3$.

Likewise as described in Example 1 there was also coated with the above diastereomer mixture a chromatography column filled with commercial silica gel particles having an average particle size of 5 μm but having the particles modified by octadecylsilane.

There was injected on the thus coated column 5 μl of a 0.1 weight percent aqueous racemic alanine solution. As the mobile phase there was employed a mixture of 15 volume percent methanol and 85 volume percent of a $10^{-4}$ molar copper II acetate solution in water. There was established a flow of 2 ml/minute. The separation was carried out at room temperature. L-alanine eluted after 5.9 minutes, D-alanine after 8.2 minutes.

What is claimed is:

1. An optically active proline derivative of the formula

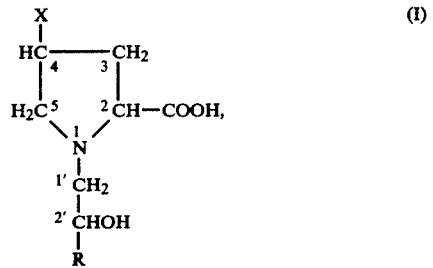

in which X is a hydrogen atom or a hydroxyl group and R is a hydrogen atom, an unsubstituted or 1–5 carbon atoms alkyl group substituted phenyl group or is an alkyl group having 1 to 20 carbon atoms.

2. An optically active proline derivative according to claim 1 where X is hydrogen.

3. An optically active proline derivative according to claim 2 where R is hydrogen or an alkyl group of 1 to 20 carbon atoms.

4. An optically active proline derivative according to claim 3 where R is hydrogen.

5. An optically active proline derivative according to claim 3 where R is an 8 to 16 carbon atom alkyl group.

6. An optically active proline derivative according to claim 2 where R is phenyl.

7. An optically active proline derivative according to claim 1 where X is a hydroxyl group.

8. An optically active proline derivative according to claim 7 where R is hydrogen or an alkyl group of 1 to 20 carbon atoms.

9. An optically active proline derivative according to claim 8 where R is hydrogen.

10. An optically active proline derivative according to claim 8 where R is an 8 to 18 carbon atom alkyl group.

11. An optically active proline derivative according to claim 7 where R is phenyl.

12. In a process of separating enantiomers by means of liquid chromatography, the improvement comprising employing a metal ion-chelate complex of an optically active proline derivative of formula (I) of claim 1 as the chiral stationary phase.

13. A process according to claim 12 wherein the metal ion is $Cu^{2+}$, $Ni^{2+}$, $Zn^{2+}$, $Cd^{2+}$, $Hg^{2+}$ or $Co^{3+}$.

14. A process according to claim 13 wherein the metal ion is $Cu^{2+}$.

15. A process according to claim 14 wherein the enantiomers are enantiomers of an alpha-aminocarboxylic acid.

16. A process according to claim 15 wherein the alpha-aminocarboxylic acid is thiazolidin-4-carboxylic acid, N-acetyl-methionine, methionine, arginine, aspartic acid, asparagine, alanine, 4,4-dimethyl-thiazolidine carboxylic acid, glutamine, isoleucine, leucine, lysine, phenylalanine, proline, serine or threonine.

17. A process according to claim 13 wherein the enantiomers are enantiomers of an alpha-aminocarboxylic acid or alpha-amino carboxylic acid derivatives selected from the group consisting of thiazolidin-4-carboxylic acid, N-acetyl-methionine, methionine, arginine, aspartic acid, asparagine, alanine, 4,4-dimethyl-thiazolidine carboxylic acid, glutamine, isoleucine, leucine, lysine, phenylalanine, proline, serine and threonine.

* * * * *